(12) United States Patent
Akbarian et al.

(10) Patent No.: US 11,712,548 B2
(45) Date of Patent: Aug. 1, 2023

(54) EUSTACHIAN TUBE DILATION CATHETER WITH DEPTH INDICIA

(71) Applicant: Acclarent, Inc., Irvine, CA (US)

(72) Inventors: Fatemeh Akbarian, Rancho Palos Verdes, CA (US); Jetmir Palushi, Irvine, CA (US)

(73) Assignee: Acclarent, Inc., Irvine, CA (US)

( * ) Notice: Subject to any disclaimer, the term of this patent is extended or adjusted under 35 U.S.C. 154(b) by 400 days.

(21) Appl. No.: 16/744,599

(22) Filed: Jan. 16, 2020

(65) Prior Publication Data

US 2020/0306513 A1 Oct. 1, 2020

Related U.S. Application Data

(60) Provisional application No. 62/825,854, filed on Mar. 29, 2019.

(51) Int. Cl.
*A61M 29/02* (2006.01)
*A61M 25/09* (2006.01)
(Continued)

(52) U.S. Cl.
CPC ............ *A61M 29/02* (2013.01); *A61M 25/09* (2013.01); *A61M 2025/0008* (2013.01);
(Continued)

(58) Field of Classification Search
CPC .. A61M 2025/0008; A61M 2025/0166; A61M 2025/09008; A61M 2025/09175;
(Continued)

(56) References Cited

U.S. PATENT DOCUMENTS

| 5,084,022 A | 1/1992 | Claude |
| 5,141,494 A | 8/1992 | Danforth et al. |
| (Continued) | | |

FOREIGN PATENT DOCUMENTS

WO WO 2012/178073 A1 12/2012

OTHER PUBLICATIONS

International Search Report and Written Opinion dated Jul. 14, 2020 for International Application No. PCT/IB2020/052647, 16 pages.

*Primary Examiner* — Mohamed G Gabr
(74) *Attorney, Agent, or Firm* — Frost Brown Todd LLP (57) ABSTRACT

A surgical system and method are used to position a guidewire within an anatomical passageway includes the guidewire, a dilator, a reference feature, and a marker. The guidewire has a guidewire body extending to a distal body end portion. The dilator is secured on the distal body end portion and configured to expand from a contracted state to an expanded state. The dilator in the contracted state is configured to pass through an isthmus of a Eustachian tube. The dilator in the expanded state is configured to dilate the Eustachian tube. The reference feature secured relative to the guidewire, and the marker is positioned on the guidewire a predetermined distance from the reference feature. Thereby, the marker is configured to indicate the predetermined distance to an operator for determining a depth of the reference feature in the anatomical passageway.

20 Claims, 5 Drawing Sheets

(51) Int. Cl.
*A61M 25/10* (2013.01)
*A61M 25/00* (2006.01)
*A61M 25/01* (2006.01)

(52) U.S. Cl.
CPC ............ *A61M 2025/0166* (2013.01); *A61M 2025/1061* (2013.01); *A61M 2029/025* (2013.01); *A61M 2205/502* (2013.01); *A61M 2210/0675* (2013.01)

(58) Field of Classification Search
CPC ........... A61M 2025/09183; A61M 2025/1061; A61M 2029/025; A61M 2205/502; A61M 2210/0675; A61M 25/0105; A61M 25/0108; A61M 25/09; A61M 29/02
See application file for complete search history.

(56) References Cited

U.S. PATENT DOCUMENTS

| | | | |
|---|---|---|---|
| 7,720,521 B2 | 5/2010 | Chang et al. | |
| 10,070,993 B2 | 9/2018 | Chan et al. | |
| 10,350,396 B2 | 7/2019 | Chan et al. | |
| 10,463,242 B2 | 11/2019 | Kesten et al. | |
| 2007/0208301 A1* | 9/2007 | Evard | A61M 29/02 604/103.1 |
| 2008/0004492 A1 | 1/2008 | Nakamura et al. | |
| 2009/0163890 A1 | 6/2009 | Clifford et al. | |
| 2010/0274188 A1 | 10/2010 | Chang et al. | |
| 2013/0274715 A1 | 10/2013 | Chan et al. | |
| 2014/0364725 A1 | 12/2014 | Makower | |
| 2015/0202089 A1 | 7/2015 | Campbell et al. | |
| 2016/0015944 A1* | 1/2016 | Jenkins | A61M 25/09041 604/528 |
| 2016/0270863 A1 | 9/2016 | Makower | |
| 2016/0287851 A1* | 10/2016 | Ha | A61B 1/0014 |
| 2017/0027724 A1 | 2/2017 | Hossainy et al. | |
| 2017/0049511 A1 | 2/2017 | Uhm et al. | |
| 2017/0119583 A1* | 5/2017 | Chan | A61B 17/32 |
| 2018/0099124 A1 | 4/2018 | McLoughlin et al. | |
| 2018/0104001 A1* | 4/2018 | Palushi | A61B 18/1206 |
| 2018/0310886 A1 | 11/2018 | Salazar et al. | |
| 2019/0015645 A1 | 1/2019 | Matlock et al. | |
| 2019/0388661 A1 | 12/2019 | Palushi et al. | |

* cited by examiner

EUSTACHIAN TUBE DILATION CATHETER WITH DEPTH INDICIA

PRIORITY

This application claims priority to U.S. Provisional Patent App. No. 62/825,854, entitled "Eustachian Tube Dilation Catheter with Depth Indicia," filed Mar. 29, 2019, the disclosure of which is incorporated by reference herein.

BACKGROUND

Figure 1:
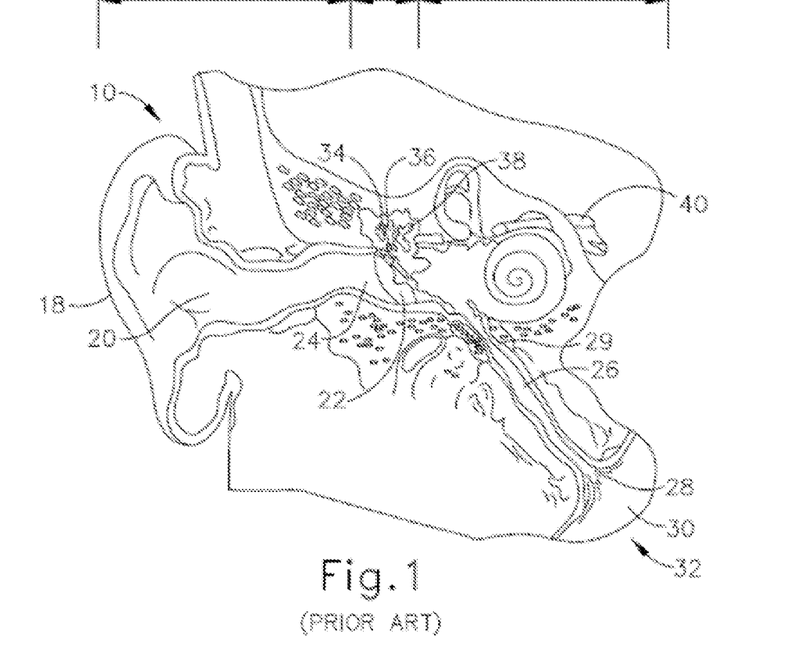
FIG. 1 depicts a cross-sectional view of a patient's head, showing the inner ear, the middle ear, the outer ear, and the Eustachian tube connecting the middle ear with the nasopharynx region of the throat.

As shown in FIG. 1, the ear (10) is divided into three parts: an external ear (12), a middle ear (14) and an inner ear (16). The external ear (12) consists of an auricle (18) and ear canal (20) that gather sound and direct it toward a tympanic membrane (22) (also referred to as the eardrum) located at an inner end (24) of the ear canal (20). The middle ear (14) lies between the external and inner ears (12, 16) and is connected to the back of the throat by a Eustachian tube (ET) (26), which serves as a pressure equalizing valve between the ear (10) and the sinuses. The ET (26) terminates in a pharyngeal ostium (28) in the nasopharynx region (30) of the throat (32). In addition to the eardrum (22), the middle ear (14) also consists of three small ear bones (ossicles): the malleus (34) (hammer), incus (36) (anvil) and stapes (38) (stirrup).

The ET (26) is a narrow channel connecting the middle ear (14) with the nasopharynx (30). The ET (26) functions as a pressure equalizing valve for the middle ear (14), which is normally filled with air. When functioning properly, the ET (26) opens for a fraction of a second periodically in response to swallowing or yawning. In so doing, it allows air into the middle ear (14) to replace air that has been absorbed by the middle ear lining (mucous membrane) or to equalize pressure changes occurring on altitude changes. Anything that interferes with this periodic opening and closing of the ET (26) may result in hearing impairment or other ear symptoms. Obstruction or blockage of the ET (26) results in a negative middle ear (14) pressure, with retraction (sucking in) of the eardrum (22). This may be accompanied by some ear discomfort, such as a fullness or pressure feeling, and may result in a mild hearing impairment and head noise (tinnitus). If the obstruction is prolonged, the middle ear (14) may eventually become infected.

Methods for treating the middle ear (14) and the ET (26) include those disclosed in U.S. Patent Pub. No. 2010/0274188, entitled "Method and System for Treating Target Tissue within the ET," published on Oct. 28, 2010, now abandoned, the disclosure of which is incorporated by reference herein; U.S. Patent Pub. No. 2013/0274715, entitled "Method and System for Eustachian Tube Dilation," published on Oct. 17, 2013, now abandoned, the disclosure of which is incorporated by reference herein; and U.S. Pat. No. 10,350,396, entitled "Vent Cap for a Eustachian Tube Dilation System," issued on Jul. 16, 2019, the disclosure of which is incorporated by reference herein. As described in those references, functioning of the ET (26) may be improved by dilating the ET (26) with an expandable dilator instrument.

While a variety of surgical instruments have been made and used, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the term "approximately" for any numerical values or ranges indicate a suitable dimensional tolerance that allows the part or collection of components to function for its intended purpose as described herein.

I. Exemplary Instrument for Dilating Eustachian Tube Via Middle Ear, and Related Surgical Navigation System With respect to FIG. 1, one example of a treatment that may be performed to treat an ET (26) that does not provide sufficient communication between the middle ear (14) and the pharyngeal ostium (28) includes accessing and dilating the ET (26) using a guide catheter and a balloon dilation catheter. However, where a guide catheter of a balloon dilation catheter cannot be used, an apparatus including a guidewire may be suitable. In other instances, it may be difficult or impossible to access the ET (26) by inserting instruments through the nostril, into the oro-nasal cavity, and through the pharyngeal ostium. This may be due to the anatomical constraints of a patient or, in some instances, to the limitations of a particular practitioner's skill set. Therefore, in some instances, it may be more efficacious to access the ET (26) through the tympanic membrane (22) and the middle ear (14). However, due to the sensitive nature of the tympanic membrane (22) and middle ear structures, it may be advantageous to access the ET (26) in a manner that preserves the integrity of the ET (26) or minimizes trauma to the ET (26). Moreover, because this approach of accessing the ET (26) requires a practitioner to direct instruments through the isthmus (29), care must be taken due to the small size and sensitive nature of the isthmus (29) and adjacent structures of the inner ear (16).

One example of a dilation instrument, such as an exemplary guidewire (300) described below with respect to FIG. 2, enables a practitioner to safely access the ET (26) via the middle ear (14) while still being operable to provide sufficient dilation of the ET (26) once positioned.

A. Exemplary Inflatable Guidewire with Markers

Figure 2:
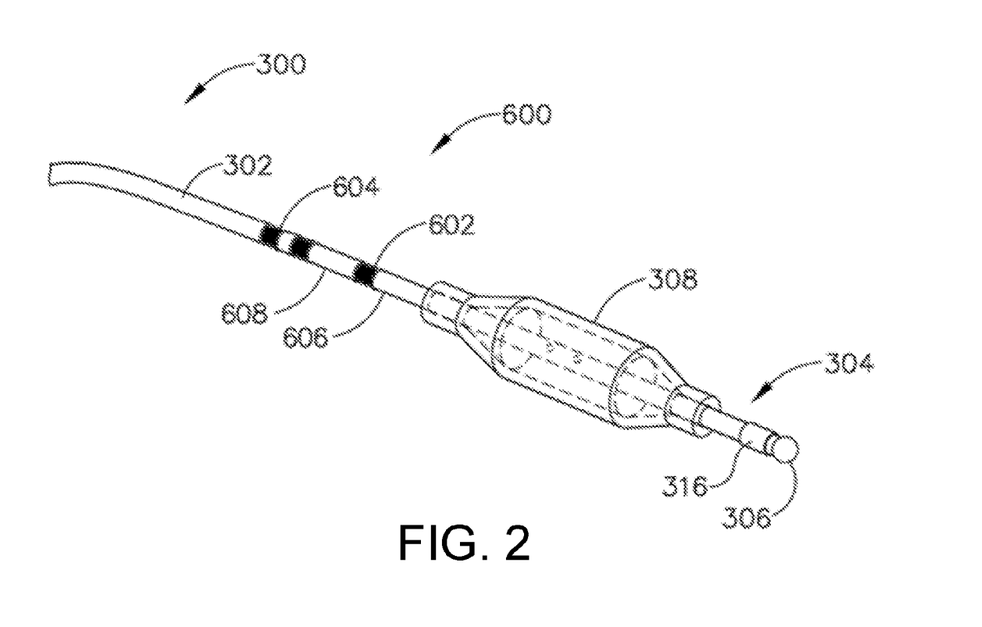
FIG. 2 depicts a perspective view of an exemplary guidewire having an inflatable balloon and a navigation sensor.

FIG. 2 shows guidewire (300) that is sized and configured to access the ET (26) through the tympanic membrane (22), the middle ear (14), and the isthmus (29). Guidewire (300) includes an elongate, tubular body (302) having a distal end portion (304), and a closed, atraumatic, distal tip (306) arranged at distal end portion (304). Atraumatic tip (306) of the present example is generally rounded in shape and is suitably sized to pass through the isthmus (29) and into the ET (26), as described in greater detail below.

Guidewire body (302) of the present example is suitably constructed with a lateral flexibility and a column strength (i.e., stiffness) sufficient to enable guidewire (300) to resiliently conform to the tortuous internal path extending between the middle ear (14) and the ET (26) of a patient without buckling or otherwise plastically deforming, and without an outer guidance device, such as a guide catheter (not shown). For instance, at least a portion of body (302) may be formed of braided stainless steel. In other examples, at least a portion of body (302) may be constructed with an outer coil (not shown) and an inner core-wire (not shown). In various examples, guidewire body (302) may be formed of one or more metal materials such as 316 stainless steel, titanium, cobalt-chrome, nitinol, MP35N steel alloy, or various other suitable materials as disclosed in U.S. Pat. No. 10,463,242, entitled "Guidewire Navigation for Sinuplasty," issued on Nov. 5, 2019, the disclosure of which is incorporated by reference herein.

Figure 3:
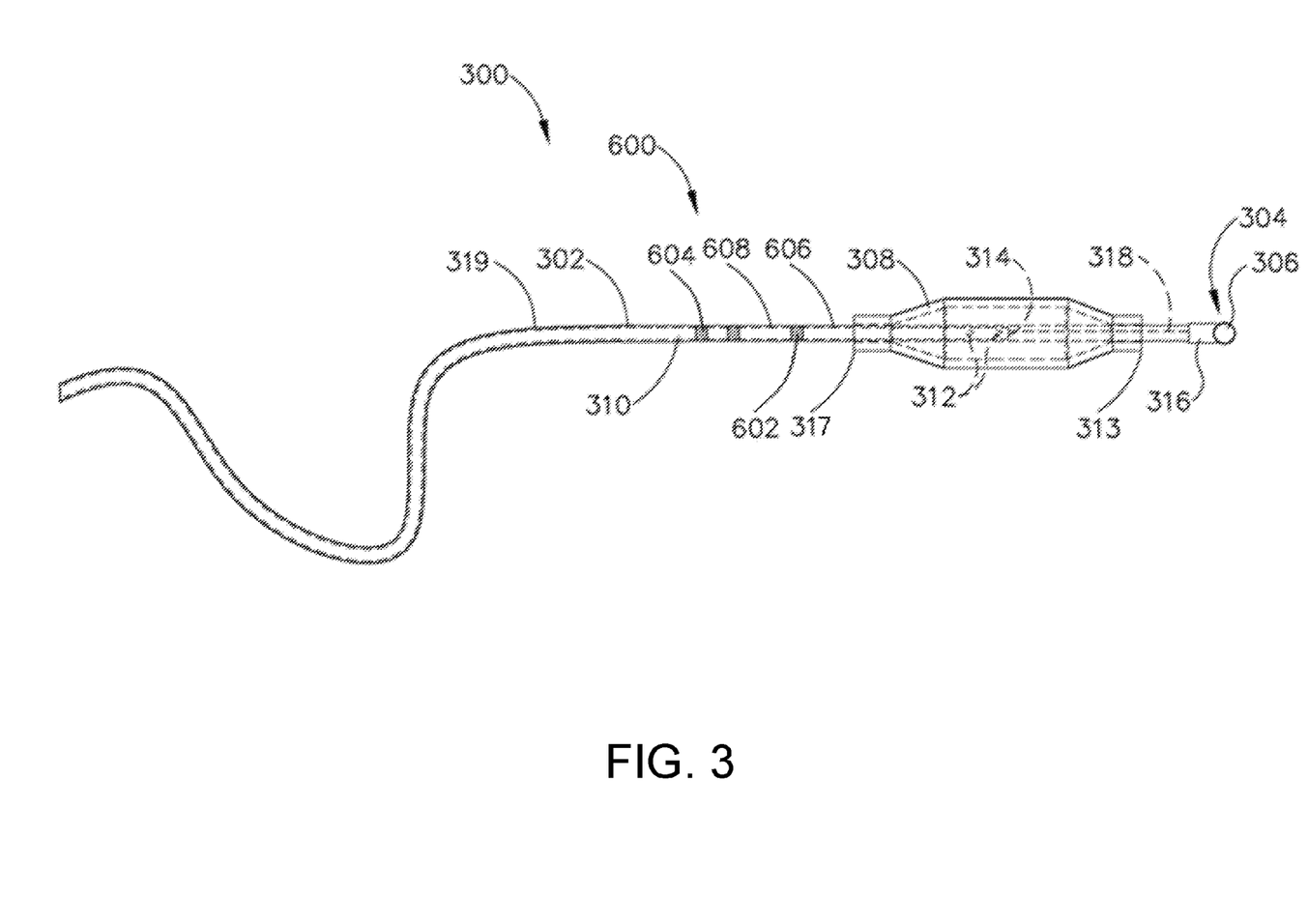
FIG. 3 depicts a side elevational view of the guidewire of FIG. 2, schematically showing an internal inflation lumen and a sensor wire of the guidewire.
Figure 5A:
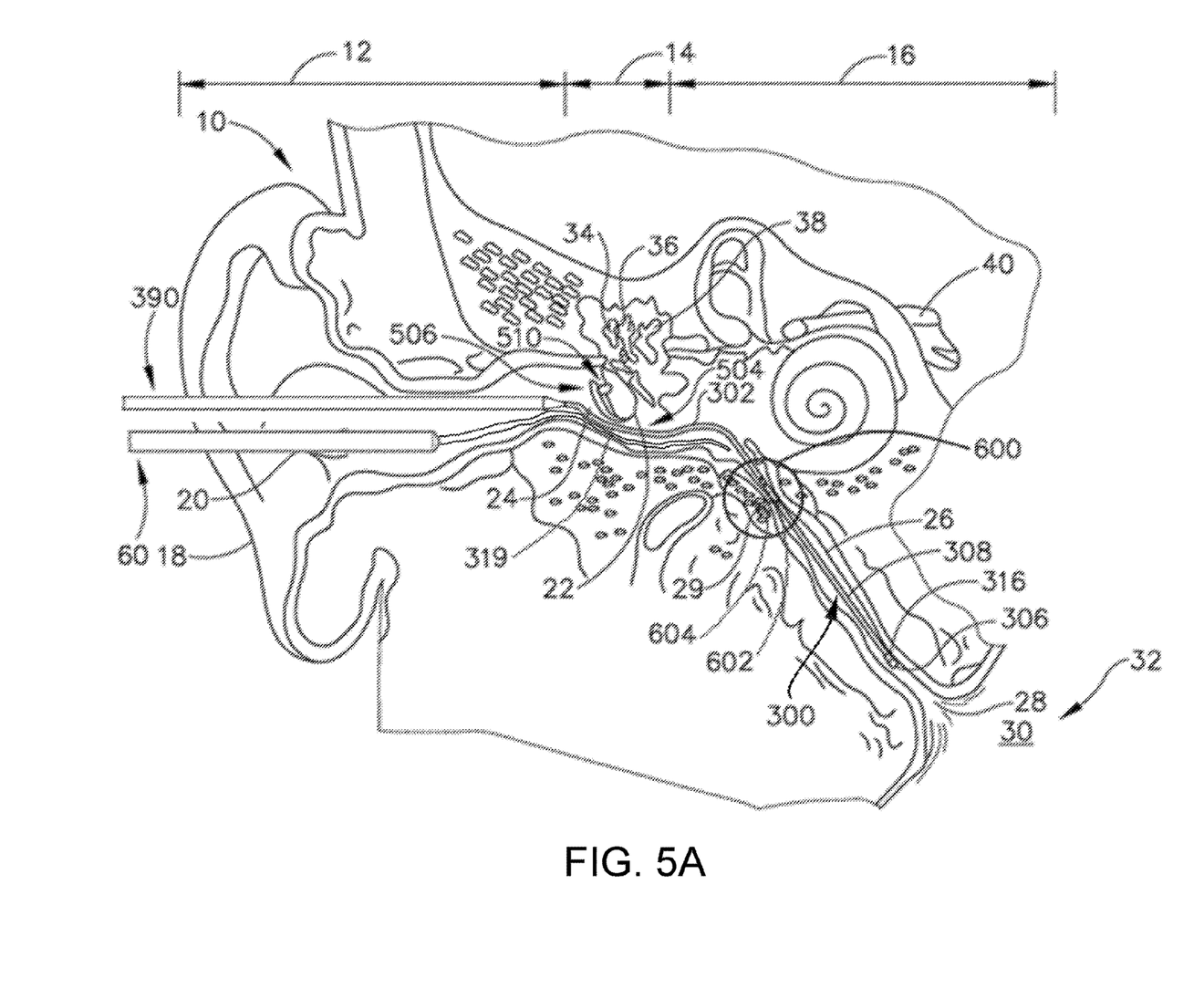
FIG. 5A depicts a cross-sectional view of a patient's head, showing a distal portion of the guidewire of FIG. 2 positioned within the patient's Eustachian tube via the middle ear.
Figure 5B:
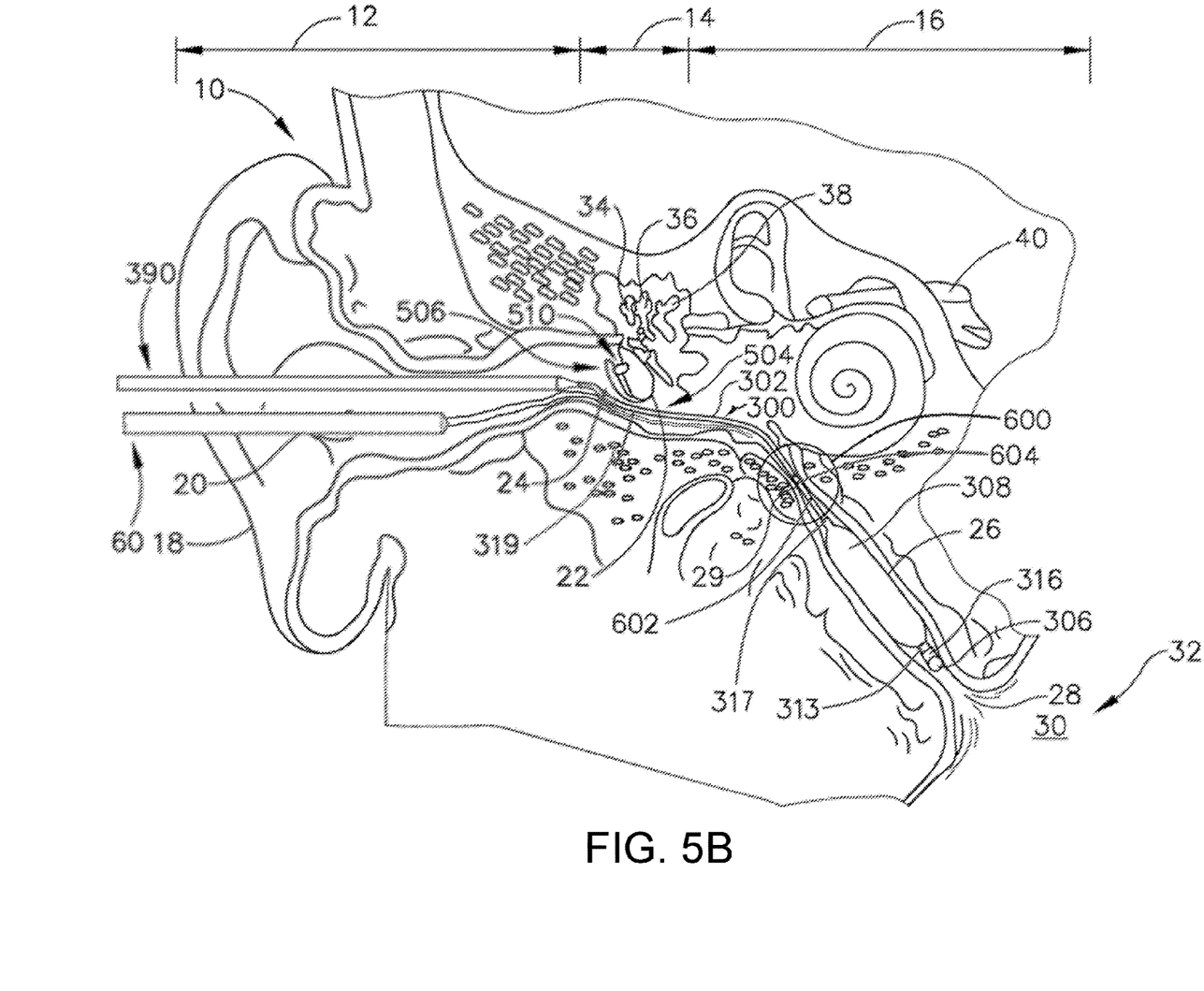
FIG. 5B depicts a cross-sectional view of the patient's head similar to FIG. 5A, but showing the balloon of the guidewire inflated to thereby dilate the Eustachian tube.

Guidewire (300) of the present example further includes an expandable dilator in the form of an inflatable balloon (308) secured to an exterior of guidewire body (302) proximal to distal tip (306). Balloon (308) may be compliant, semi-compliant, or non-compliant in construction, and may be formed of any suitable polymeric material such as polyethylene terepthalate (PET), PEBAX® (polyether block amide), nylon, or the like. Balloon (308) of the present example is suitably sized and configured to provide guidewire (300) with a maximum outer diameter of less than or equal to approximately 1 millimeter when balloon (308) is deflated, as shown in FIG. 5A, and a maximum outer diameter of approximately 6 millimeters or greater when balloon (308) is fully inflated, as shown in FIGS. 2-3 and 5B. In at least some applications, a maximum outer diameter of approximately 6 millimeters provides sufficient dilation of a patient's ET (26) during an ET dilation procedure. It will be appreciated, however, that balloon (308) may be suitably configured to assume other maximum sizes for use in other applications and dilation procedures. Balloon (308) of the present example may have a working length of approximately 12 millimeters to approximately 24 millimeters. In other examples, balloon (308) may have a working length of approximately 20 millimeters to approximately 40 millimeters.

As shown best in FIG. 3, an internal inflation lumen (310) extends longitudinally through guidewire body (302) along the central longitudinal axis of body (302). A proximal end portion (not shown) of inflation lumen (310) fluidly communicates with an inflation medium source (not shown). A distal end of inflation lumen (310) fluidly communicates with an interior of balloon (308) via a plurality of apertures (312) that extend laterally through a sidewall of guidewire body (302). While guidewire body (302) of the present example includes four apertures (312) approximately aligned with a medial portion of balloon (308), any suitable quantity and arrangement of apertures (312) may be provided in other examples. Inflation lumen (310) terminates at a distal wall (314) located distal to the distal-most aperture (312) and proximal to a distal end (313) of balloon (308). Inflation lumen (310) is configured to communicate a pressurized medium (e.g., saline) to and from the interior of balloon (308) in response to user input to enable selective inflation and deflation during a dilation procedure, such as described below in one example described with reference to FIGS. 5A-5B.

Though not shown, guidewire (300) may be actuated with an actuating device of any suitable type that may be held and operated by a user, and which may have features similar to those disclosed in U.S. Pat. Pub. No. 2019/0015645, entitled "Adjustable Instrument for Dilation of Anatomical Passageway," published Jan. 17, 2019, issued as U.S. Pat. No. 10,874,839 on Dec. 29, 2020, the disclosure of which is incorporated by reference herein.

Guidewire (300) of the present example shown in FIG. 3 further includes a navigation sensor (316) (shown schematically) arranged at distal end portion (304) proximal to distal tip (306) and distal to the distal end (313) of balloon (308). Navigation sensor (316) is operable to generate signals corresponding to the location of distal end portion (304) within a patient during a surgical procedure, and thus enables a surgeon to track the location of distal end portion (304) within the patient in real time, as described in greater detail below. Navigation sensor (316) may be in the form of an electrically conductive coil (not shown) configured to generate an electrical signal when placed within an externally generated magnetic field, as described below.

As shown in FIG. 3, guidewire (300) houses a pair of sensor wires (318) that couple to navigation sensor (316) and extend proximally through distal lumen wall (314) and inflation lumen (310) toward proximal end portion (not shown) of guidewire (300). The location at which sensor wires (318) extend through distal lumen wall (314) may be sealed with an adhesive (not shown) or other material suitable to prevent ingress of inflation fluid from lumen (310) toward navigation sensor (316). Accordingly, navigation sensor (316) is fluidically isolated from inflation lumen (310). Sensor wires (318) are configured to communicate electrical signals from navigation sensor (316) to the processor of a navigation system, such as processor (408) (see FIG. 4) of surgical navigation system (401) described below. While only one navigation sensor (316) is shown, two or more navigation sensors may be provided in other examples at various locations within guidewire (300), for instance to track both a location and a rotational orientation of distal end portion (304) of guidewire (300) within the patient. It will be appreciated, however, that navigation sensor (316) is merely optional and may be entirely omitted from guidewire (300) in some examples, as well as sensor wires (318). In such examples, guidewire (300) may be navigated through the anatomical passages of a patient with the assistance of various other suitable guidance devices and methods disclosed below, those readily apparent to those skilled in the art, or without any such guidance devices.

Guidewire (300) further includes a marker pattern (600) including one or more markers (602, 604) near distal end portion (304) of guidewire (300), such as being located proximate to a proximal end (317) of balloon (308), and one or more partitions (606, 608) to separate markers (602, 604). In the present example, such markers (602, 604) are depth indicia configured to visually indicate how far a reference feature, such as a proximal end (317) of balloon (308), is located inside a desired anatomy of the patient. Such reference feature is secured to body (302) a predetermined distance from each such marker (602, 604), respectively. Markers (602, 604) are thus positioned fixed, longitudinal distances from reference feature, which in the present example is more particularly proximal end (317) of balloon (308). Markers (602, 604) shown in the present example are etched, such as by lasers, directly onto an outer surface (319) of body (302), but alternative markers (not shown) may be positioned on body (302) by other known methods, such as fasteners or coloring.

When guidewire (300) is advanced through an anatomical passageway, such as within ear (10) (see FIG. 5A) markers (602, 604) are located and checked under endoscopic vision to determine with high accuracy, how far guidewire (300) is advanced within the anatomical passageway. Markers (602, 604) could be visible under microscope, endoscopic view, or any other suitable means. Patterns using one or more markers (602, 604) may also indicate the distance guidewire (300) is within the anatomical passageway, such as having one marker (602, 604) one centimeter within the cavity, two markers (602, 604) two centimeters within the cavity, and so on. Alternatively, one marker, (602, 604) could be located at each centimeter increment from the proximate end of balloon (308) on guidewire (300). Of course, markers (602, 604) may be located at any known location on body (302) of guidewire (300) relative to any predetermined reference feature such that the invention is not intended to be unnecessarily limited to the particular markers (602, 604) and partitions (606, 608) shown and described herein. Thus, any unit of distance suitable for the application could be used and any number of markers (602, 604) may be located on guidewire (300).

B. Exemplary Surgical Navigation System Incorporating Guidewire with Marker

Figure 4:
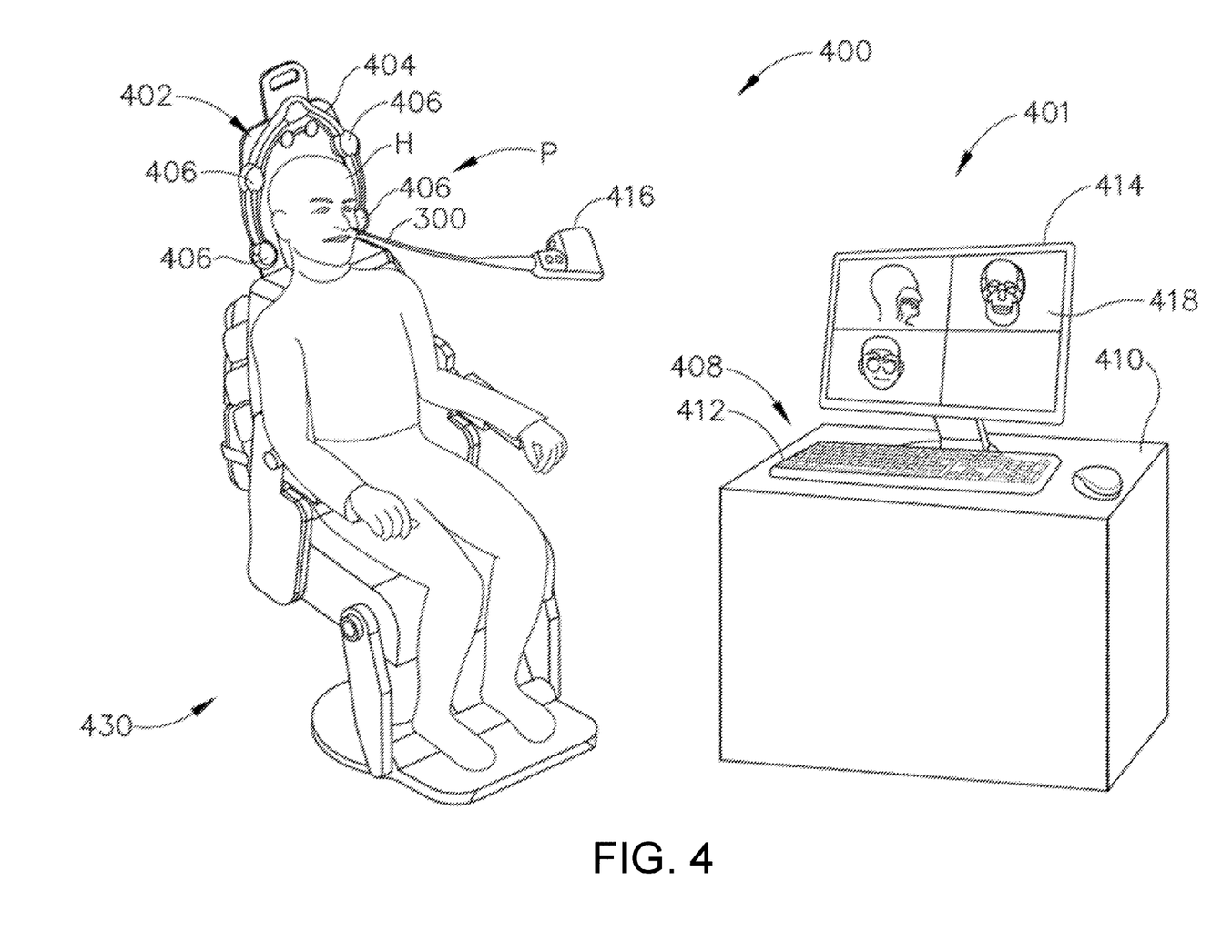
FIG. 4 depicts a schematic perspective view of an exemplary surgical navigation system that incorporates the guidewire of FIG. 2.

FIG. 4 shows an exemplary surgical system (400) incorporating guidewire (300 and an exemplary IGS navigation system (401) enabling an ENT procedure to be performed using image guidance. When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). In addition to or in lieu of having the components and operability described herein IGS navigation system (401) may be constructed and operable in accordance with at least some of the teachings of U.S. Pat. No. 7,720,521, entitled "Methods and Devices for Performing Procedures within the Ear, Nose, Throat and Paranasal Sinuses," issued on May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IGS navigation system (401) of the present example comprises a field generator assembly (402), which comprises set of magnetic field generators (406) that are integrated into a horseshoe-shaped frame (404). Field generators (406) are operable to generate alternating magnetic fields of different frequencies around the head (H) of the patient (P). Guidewire (300) is inserted into the head (H) of the patient (P) in this example. In the present example, frame (404) is mounted to a chair (430), with the patient (P) being seated in chair (430) such that frame (404) is located adjacent to the head (H) of the patient (P). By way of example only, chair (430) and/or field generator assembly (402) may be configured and operable in accordance with at least some of the teachings of U.S. Pub. No. 2018/0310886, entitled "Apparatus to Secure Field Generating Device to Chair," published Nov. 1, 2018, issued as U.S. Pat. No. 10,561,370 on Feb. 18, 2020, the disclosure of which is incorporated by reference herein.

IGS navigation system (401) of the present example further comprises a processor (408), which controls field generators (406) and other elements of IGS navigation system (401). For instance, processor (408) is operable to drive field generators (406) to generate alternating electromagnetic fields; and process signals from navigation guidewire (300) to determine the location of sensor (316) (see FIG. 2) in guidewire (300) within the head (H) of the patient (P). Processor (408) comprises a processing unit (not shown) communicating with one or more memories (not shown). Processor (408) of the present example is mounted in a console (410), which comprises operating controls (412) that include a keypad and/or a pointing device such as a mouse or trackball. An operator, such as a physician, uses operating controls (412) to interact with processor (408) while performing the surgical procedure.

Guidewire (300) includes sensor (316) (see FIG. 2) that is responsive to positioning within the alternating magnetic fields generated by field generators (406). A communication unit (416) is secured to the proximal end of guidewire (300) and is configured to provide communication of data and other signals between console (410) and guidewire (300). Communication unit (416) may provide wired or wireless communication of data and other signals.

In the present example, sensor (316) (see FIG. 2) of guidewire (300) comprises at least one coil (not shown) at a distal end of navigation guidewire (14). When such a coil (not shown) is positioned within an alternating electromagnetic field generated by field generators (406), the alternating magnetic field may generate electrical current in the coil (not shown), and this electrical current may be communicated along electrical wires (318) (see FIG. 3) in guidewire (300) and further to processor (408) via communication unit (416). This phenomenon may enable IGS navigation system (401) to determine the location of distal end portion (304) (see FIG. 2) of guidewire (300) or other medical instrument (e.g., dilation instrument, surgical cutting instrument, etc.) within a three-dimensional space (i.e., within the head (H) of the patient (P), etc.). To accomplish this, processor (408) executes an algorithm to calculate location coordinates of distal end portion (304) of guidewire (300) from the position related signals of the coil(s) (not shown) in guidewire (300). While sensor (316) (see FIG. 2) is located in guidewire (300) in this example, such a position sensor may be integrated into various other kinds of instruments.

Processor (408) uses software stored in the memory (not shown) of processor (408) to calibrate and operate IGS navigation system (401). Such operation includes driving field generators (406), processing data from guidewire (300), processing data from operating controls (412), and driving a display screen (414). In some implementations, operation may also include monitoring and enforcement of one or more safety features or functions of IGS navigation system (401). Processor (408) is further operable to provide video in real time via display screen (414), showing the position of distal end portion (304) (see FIG. 2) of guidewire (300) in relation to a video camera image of the patient's head (H), a CT scan image of the patient's head (H), and/or a computer-generated three-dimensional model of the anatomy within and adjacent to the patient's nasal cavity. Display screen (414) may display such images simultaneously and/or superimposed on each other during the surgical procedure. Such displayed images may also include graphical representations of instruments that are inserted in the patient's head (H), such as navigation guidewire (14), such that the operator may view the virtual rendering of the instrument at its actual location in real time. By way of example only, display screen (414) may provide images in accordance with at least some of the teachings of U.S. Pat. No. 10,463,242, entitled "Guidewire Navigation for Sinuplasty," issued on Nov. 5, 2019, the disclosure of which is incorporated by reference herein. In the event that the operator is also using an endoscope, the endoscopic image may also be provided on display screen (414).

The images provided through display screen (414) may help guide the operator in maneuvering and otherwise manipulating instruments within the patient's head (H) when such instruments incorporate guidewire (300). It should also be understood that other components of a surgical instrument and other kinds of surgical instruments, as described herein, may incorporate a sensor like sensor (316) (see FIG. 2) of guidewire (300).

C. Exemplary Method of Dilating Eustachian Tube Using Guidewire with Marker

FIGS. 5A-5B show an exemplary method of dilating the ET (26) of a patient using guidewire (300) described above. Rather than inserting guidewire (300) through a nostril, into the nasal cavity, and through the pharyngeal ostium (28), the method shown in FIGS. 5A-5B includes accessing the ET (26) through the ear canal (20) and the tympanic membrane (22). In the present example shown in FIG. 5A, guidewire (300) is advanced through ear canal (20) and navigated through the internal passageways of the patient's head with real-time guidance provided by navigation sensor (316) and IGS navigation system (401) as described above. Guidewire (300) is shown extending from a proximal shaft (390) disposed in ear canal (20). Some variations may omit proximal shaft (390) such guidewire (300) with balloon (308) extending into ear canal (20) without shaft (390). As also described above, navigation sensor (316) is merely optional. Accordingly, in other examples, guidewire (300) may be employed to access and dilate the ET (26) with alternative types of guidance features, such as an endoscope or an illuminating fiber (not shown), or even without any such guidance features.

Those of ordinary skill in the art will recognize that the tympanic membrane (22) provides a physical barrier to passage of an instrument, such as balloon catheter, from the ear canal (20) into the ET (26). Thus, an operator must somehow address the presence of the tympanic membrane (22) in order to gain access to the ET (26) from the ear canal (20). One such exemplary method passing the tympanic membrane (22) in order to suitably insert guidewire (300) into the ET (26) via the ear canal (20) is disclosed in U.S. Pat. No. 10,070,993, entitled "System and Method for Treatment of Eustachian Tube from Middle Ear Approach," issued on Sep. 11, 2018, the disclosure of which is incorporated by reference herein.

The operator continues to insert balloon (308) distally beyond the middle ear (14) and ET (26) without compromising the integrity of the tympanic membrane (22). In the present example, an endoscope (60) is inserted alongside guidewire (300) into the middle ear (14) in order to provide visualization of guidewire (300) positioned in isthmus (29). Additional teachings associated within placement of endoscope (60) in middle ear (14) are disclosed in U.S. Pat. Pub. No. 2019/0388661, entitled "Guidewire for Dilating Eustachian Tube Via Middle Ear," published Dec. 26, 2019, issued as U.S. Pat. No. 11,033,721 on Jun. 15, 2021, the disclosure of which is incorporated by reference herein.

The operator distally advances balloon (308) into ET (26) toward a target position for expanding balloon (308) from a contacted state to an expanded state to thereby dilate ET (26). In order to more accurately and precisely position balloon (308) in the target position, the operator simultaneously views the visualization of markers (602, 604) relative to isthmus (29) or other adjacent reference anatomy. In one example, with each marker (602, 604) proximally positioned from balloon (308) indicating an additional, respective centimeter from balloon (308), the operator counts the passage of each marker (602, 604) passing beyond isthmus (29). In turn, the operator determines the distance between the last visible marker (602, 604) proximally positioned relative to isthmus (29) and proximal end (317) of balloon (308), which is the reference feature in the present example. The operator may count one marker (602), which is one centimeter from proximal end (317) of balloon (308), passing distally beyond isthmus (29) while another marker (604), which is two centimeters from proximal end (317) of balloon (308), remains visible adjacent to isthmus (29). The operator may then determine that proximal end (317) of balloon (308) is approximately two centimeters from isthmus (29) without directly viewing proximal end (317) of balloon (308). Similar determinations may be made by the operator based on the particular patterns on markers (602, 604) in other examples.

Furthermore, in one example with further reference to FIGS. 3 and 4, the operator may view display (414) for a position of sensor (316) on guidewire (300) while also viewing the visualization of markers (602, 604) discussed above. Such viewing may be beneficial for locating the distal end portion (304) of guidewire (300) on display (414) while identifying proximal end (317) of balloon (308) in the ET (29) for corroborating the position of balloon (308) in ET (29) for more accurate and precise positioning of balloon (308) in the desired, target position. In any case, once in the target position within the ET (ET), the operator expands balloon (308) from the contracted state shown in FIG. 5A to the expanded state shown in FIG. 5B, thereby dilating the ET. Once expanded, the operator may return balloon (308) to the contracted state for removal or repositioning for another dilation as desired. Such repositioning may again be performed based on visualization of markers (602, 604) and/or display (414).

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical system, comprising: (a) a guidewire including a guidewire body extending to a distal body end portion thereof; (b) a dilator secured on the distal body end portion and configured to expand from a contracted state to an expanded state, wherein the dilator in the contracted state is configured to pass through an isthmus of a Eustachian tube, and wherein the dilator in the expanded state is configured to dilate the Eustachian tube; (c) a reference feature secured relative to the guidewire; and (d) a first marker positioned on the guidewire a first predetermined distance from the reference feature and configured to indicate the first predetermined distance to an operator for determining a depth of the reference feature in an anatomical passageway.

Example 2

The surgical system of Example 1, wherein the reference feature is a portion of the dilator.

Example 3

The surgical system of Example 2, wherein the portion of the dilator is a proximal end of the dilator.

Example 4

The surgical system of any one or more of Examples 1 through 3, wherein the first marker is positioned on the guidewire body of the guidewire.

Example 5

The surgical system of Example 4, wherein the guidewire body has an outer surface and the first marker is positioned on the outer surface.

Example 6

The surgical system of Example 5, wherein the first marker is a first etched maker on the outer surface.

Example 7

The surgical system of any one or more of Examples 1 through 6, wherein the reference feature is distally positioned relative to the first marker the first predetermined distance.

Example 8

The surgical system of any one or more of Examples 1 through 7, further comprising a second marker positioned on the guidewire a second predetermined distance from the reference feature and configured to indicate the second predetermined distance to the operator for further determining the depth of the reference feature in the anatomical passageway.

Example 9

The surgical system of Example 8, wherein the reference feature is distally positioned relative to the first marker the first predetermined distance, and wherein the reference feature is distally positioned relative to the second marker the second predetermined distance.

Example 10

The surgical system of Example 9, wherein the second predetermined distance is greater than the first predetermined distance.

Example 11

The surgical system of any one or more of Examples 1 through 10, wherein the distal body end portion has a closed distal tip.

Example 12

The surgical system of any one or more of Examples 1 through 11, wherein the guidewire with the dilator in the contracted state defines a contracted diameter radially about the guidewire body, and wherein the contracted diameter is less than or equal to one millimeter.

Example 13

The surgical system of any one or more of Examples 1 through 12, wherein the guidewire with the dilator in the expanded state defines an expanded diameter radially about the guidewire body, and wherein the expanded diameter is less than or equal to six millimeters.

Example 14

The surgical system of any one or more of Examples 1 through 13, further comprising a navigation sensor secured relative to the guidewire and configured to generate a signal to be detected by a navigation system for determined a position of the navigation sensor within a patient.

Example 15

The surgical system of Example 14, further comprising a processor in communication with the navigation sensor, wherein the processor is configured to receive the signal generated by the navigation sensor and determine with position of the navigation sensor within the patient.

Example 16

A guidewire, comprising: (a) a guidewire body having an outer surface and extending to a distal body end portion thereof, wherein the distal body end portion has a closed distal tip; (b) a dilator secured on the distal body end portion and configured to expand from a contracted state to an expanded state, wherein the dilator in the contracted state is configured to pass through an isthmus of a Eustachian tube, and wherein the dilator in the expanded state is configured to dilate the Eustachian tube; (c) a reference feature secured relative to the guidewire body; and (d) a first marker on the outer surface of the guidewire body proximally positioned a first predetermined distance from the reference feature and configured to indicate the first predetermined distance to an operator for determining a depth of the reference feature in an anatomical passageway.

Example 17

The guidewire of Example 16, further comprising a second marker on the outer surface of the guidewire proximally positioned a second predetermined distance from the reference feature and configured to indicate the second predetermined distance to the operator for further determining the depth of the reference feature in the anatomical passageway.

Example 18

The guidewire of Example 17, wherein the second predetermined distance is greater than the first predetermined distance.

Example 19

A method of positioning a guidewire within an anatomical passageway, comprising viewing a marker on a guidewire body of the guidewire within the anatomical passageway thereby identifying the position of a dilator secured on the guidewire within the anatomical passageway.

Example 20

The method of Example 19, wherein the anatomical passageway is a Eustachian tube, and the method further comprises inserting the dilator along the Eustachian tube to a target position based on the viewed marker.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical system, comprising:
   (a) a guidewire including a guidewire body extending to a distal body end portion thereof, wherein the distal body end portion terminates into an atraumatic distal tip;
   (b) a dilator secured on the distal body end portion and configured to expand from a contracted state to an expanded state, wherein the dilator, in the contracted state, and the atraumatic distal tip are configured to pass through an isthmus of a Eustachian tube from a middle ear, and wherein the dilator in the expanded state is configured to dilate the Eustachian tube;
   (c) a reference feature secured relative to the guidewire; and
   (d) a first marker positioned on the guidewire a first predetermined distance from the reference feature and configured to indicate the first predetermined distance to an operator for determining a depth of the reference feature in an anatomical passageway.

2. The surgical system of claim 1, wherein the reference feature is a portion of the dilator.

3. The surgical system of claim 2, wherein the portion of the dilator is a proximal end of the dilator.

4. The surgical system of claim 1, wherein the first marker is positioned on the guidewire body of the guidewire.

5. The surgical system of claim 4, wherein the guidewire body has an outer surface and the first marker is positioned on the outer surface.

6. The surgical system of claim 5, wherein the first marker is a first etched maker on the outer surface.

7. The surgical system of claim 1, wherein the reference feature is distally positioned relative to the first marker the first predetermined distance.

8. The surgical system of claim 1, further comprising a second marker positioned on the guidewire a second predetermined distance from the reference feature and configured to indicate the second predetermined distance to the operator for further determining the depth of the reference feature in the anatomical passageway.

9. The surgical system of claim 8, wherein the reference feature is distally positioned relative to the first marker the first predetermined distance, and wherein the reference feature is distally positioned relative to the second marker the second predetermined distance.

10. The surgical system of claim 9, wherein the second predetermined distance is greater than the first predetermined distance.

11. The surgical system of claim 1, wherein the distal body end portion has a closed distal tip.

12. The surgical system of claim 1, wherein the guidewire with the dilator in the contracted state defines a contracted diameter radially about the guidewire body, and wherein the contracted diameter is less than or equal to one millimeter.

13. The surgical system of claim 1, wherein the guidewire with the dilator in the expanded state defines an expanded diameter radially about the guidewire body, and wherein the expanded diameter is less than or equal to six millimeters.

14. The surgical system of claim 1, further comprising a navigation sensor secured relative to the guidewire and configured to generate a signal to be detected by a navigation system for determined a position of the navigation sensor within a patient.

15. The surgical system of claim 14, further comprising a processor in communication with the navigation sensor, wherein the processor is configured to receive the signal generated by the navigation sensor and determine with position of the navigation sensor within the patient.

16. A guidewire, comprising:
   (a) a guidewire body having an outer surface and extending to a distal body end portion thereof, wherein the distal body end portion has a closed distal tip;
   (b) a dilator secured on the distal body end portion and configured to expand from a contracted state to an expanded state, wherein the dilator, in the contracted state, and the closed distal tip are configured to pass through an isthmus of a Eustachian tube while actuating toward a pharyngeal ostium adjacent to the Eustachian tube, and wherein the dilator in the expanded state is configured to dilate the Eustachian tube;
   (c) a reference feature secured relative to the guidewire body; and
   (d) a first marker on the outer surface of the guidewire body proximally positioned a first predetermined distance from the reference feature and configured to indicate the first predetermined distance to an operator for determining a depth of the reference feature in an anatomical passageway.

17. The guidewire of claim 16, further comprising a second marker on the outer surface of the guidewire proximally positioned a second predetermined distance from the reference feature and configured to indicate the second predetermined distance to the operator for further determining the depth of the reference feature in the anatomical passageway.

18. The guidewire of claim 17, wherein the second predetermined distance is greater than the first predetermined distance.

19. A method of positioning a guidewire within an anatomical passageway, comprising:
   (a) inserting a distal tip of the guidewire and a dilator secured to the guidewire into a middle ear of a patient;
   (b) further inserting the distal tip and the dilator, while in a deflated configuration, through an isthmus of the patient such that the dilator is within a Eustachian tube of the patient;
   (c) viewing a marker on a guidewire body of the guidewire within the middle ear of the patient thereby identifying the position of the dilator secured on the guidewire within the Eustachian tube.

20. The method of claim 19, further comprising inserting the dilator along the Eustachian tube to a target position based on the viewed marker.

* * * * *